United States Patent [19]

Zahir et al.

[11] Patent Number: 4,801,660
[45] Date of Patent: Jan. 31, 1989

[54] COMPOSITIONS COMPRISING AN EPOXY RESIN AND MERCAPTAN-CONTAINING POLYPHENOLS

[75] Inventors: Abdul-Cader Zahir, Oberwil; Karl Mechera, Muttenz, both of Switzerland

[73] Assignee: Ciba-Geigy Corporation, Ardsley, N.Y.

[21] Appl. No.: 110,163

[22] Filed: Oct. 19, 1987

Related U.S. Application Data

[62] Division of Ser. No. 3,962, Jan. 16, 1987, Pat. No. 4,721,814.

[30] Foreign Application Priority Data

Jan. 23, 1986 [CH] Switzerland ............ 253/86

[51] Int. Cl.[4] ............ C08L 63/02; C08L 61/14
[52] U.S. Cl. ............ 525/481; 525/523; 528/99
[58] Field of Search ............ 568/62, 66, 29, 39; 525/48, 523, 528; 528/99

[56] References Cited

U.S. PATENT DOCUMENTS

| | | | |
|---|---|---|---|
| 3,336,393 | 8/1967 | Weil et al. ............ | 568/29 |
| 3,506,716 | 4/1970 | Peterli et al. ............ | 524/333 |
| 3,546,163 | 12/1970 | Peterli et al. ............ | 524/333 |
| 3,729,443 | 4/1973 | Peterli et al. ............ | 524/333 |
| 3,940,374 | 2/1976 | Oswald et al. ............ | 568/66 |
| 4,055,539 | 10/1977 | Rosenberger ............ | 568/4 |

FOREIGN PATENT DOCUMENTS

| | | | |
|---|---|---|---|
| 1074865A | 2/1984 | U.S.S.R. ............ | 568/62 |
| 0959123 | 5/1964 | United Kingdom ............ | 568/39 |

*Primary Examiner*—John C. Bleutge
*Assistant Examiner*—Robert E. L. Sellers, II
*Attorney, Agent, or Firm*—Harry Falber

[57] ABSTRACT

Compounds of formula I or II

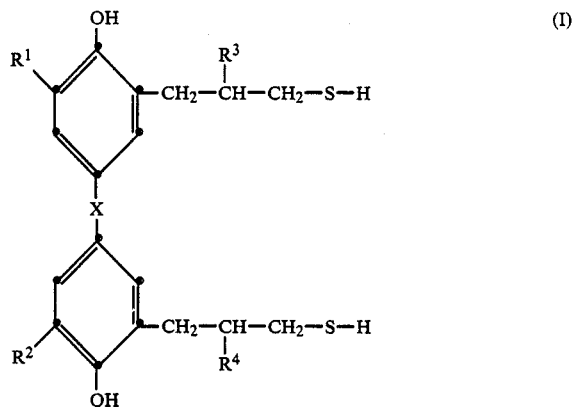

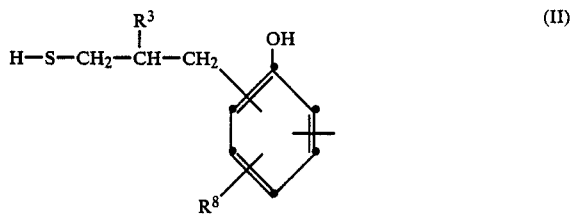

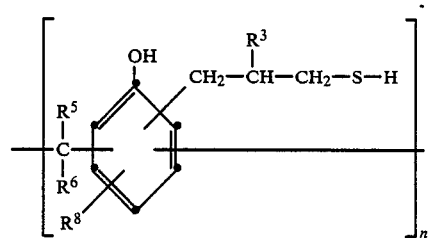

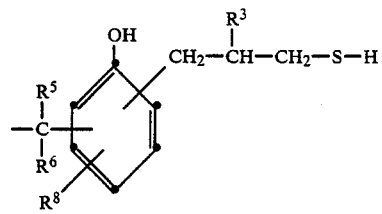

in which formulae $R^1$ and $R^2$ are each independently of the other hydrogen, alkyl, alkenylmethyl, cyclohexyl, phenyl, benzyl or tolyl, or are a —$CH_2$—$CHR^3$—$CH_2$—S—H group, $R^3$ and $R^4$ are each independently of the other hydrogen or methyl, X is alkylene, —S—, —SO—, —$SO_2$— or substituted alkylene, $R^5$ and $R^6$ are each independently of the other hydrogen or alkyl, $R^8$ is hydrogen, alkyl, alkenylmethyl or phenyl, and wherein n is an integer from 1 to 10, can be used as hardeners for epoxy resins.

The compositions containing epoxy resins and these hardeners are particularly suitable for use as adhesive formulations. The cured products have good moisture resistance.

2 Claims, No Drawings

COMPOSITIONS COMPRISING AN EPOXY RESIN AND MERCAPTAN-CONTAINING POLYPHENOLS

This is a divisional of application Ser. No. 003,962 filed on Jan. 16, 1987 now U.S. Pat. No. 4,721,814.

The present invention relates to compounds containing at least two mercaptan radicals and phenolic hydroxyl groups, to compositions containing a curable epoxy resin and said compounds, to the cured products which can be obtained therefrom and to the use of the curable compositions as adhesives.

Epoxy resins are well known in the art and are reacted with a wide range of different hardeners to form cured products.

Bismercaptan hardeners are konwn. As a rule, these compounds are acitve even at room temperature. For many applications a curing reaction which can be carrried out under controlled temperature conditions is desirable. In accordance with the present invention, this can be achieved by employing a mercaptan hardener containing a second, less reactive, phenolic hydroxyl group in the molecule.

The cured product adheres particularly well to metals and has very good moisture resistance.

Mercaptpropylphenols are known from U.S. Pat. No. 3,336,393 as pesticides. No mention of the use thereof as hardeners for epoxy resins is made in said patent specification. Moreover, the known compounds are mononuclear monophenols.

The present invention relates to compounds of formula I or II

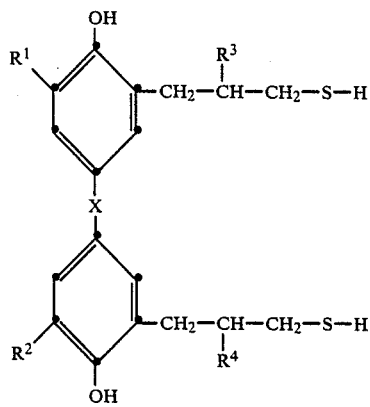

(I)

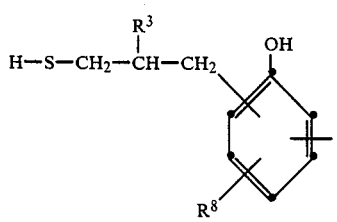

(II)

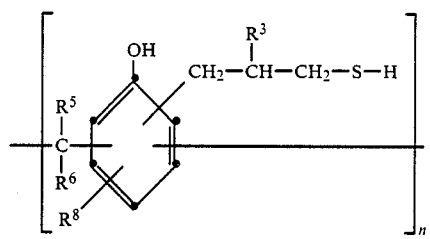

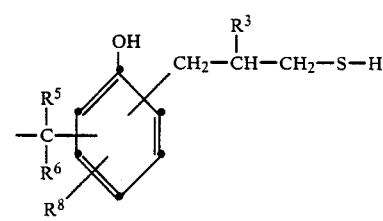

in which formulae $R^1$ and $R^2$ are each independently of the other hydrogen, $C_1$-$C_{18}$alkyl, $C_3$-$C_{18}$alkenylmethyl, cyclohexyl, phenyl, benzyl or tolyl, or are a —$CH_2$—$CHR^3$—$CH_2$—S—H group, $R^3$ and $R^4$ are each independently of the other hydrogen or methyl, X is —$CR^5R^6$—, —S—, —SO—, —$SO_2$— or —($CH_3$)-C[—($CH_2$)$_m$—$COOR^7$]—, $R^5$ and $R^6$ independently of the other hydrogen or $C_1$-$C_6$alkyl, $R^7$ is $C_1$-$C_{18}$-alkyl, $R^8$ is hydrogen, $C_1$-$C_{18}$alkyl, $C_3$-$C_{18}$alkenylmethyl or phenyl, m is 1 or 2 and n is an integer from 1 to 10.

$R^1$, $R^2$, $R^7$ and $R^8$ as $C_1$-$C_{18}$alkyl are straight chain or branche preferably straight chain, radicals. Illustrative of such radicals are methyl, ethyl, propyl, isopropyl, n-butyl, sec-butyl, tertbutyl, n-pentyl, n-hexyl, n-heptyl, n-octyl, n-nonyl, n-decyl, n-dodecyl, n-tetradecyl, n-hexadecyl or n-octadecyl, as well as 1,1,3,3-tetramethylbutyl or 2-ethylhexyl.

Short and straight chain $C_1$-$C_6$alkyl radicals are preferred, with methyl being most preferred.

$R^5$ and $R^6$ as $C_1$-$C_6$alkyl may be e.g. methyl, ethyl, n-propyl, n-butyl, n-pentyl or n-hexyl, with methyl being preferred.

$R^1$, $R^2$ and $R^3$ as $C_3$-$C_{18}$alkenylmethyl radicals are straight chain or branched, preferably straight chain. Examples of such radiicals are allyl, but-3-enyl, pent-4-enyl, hex-5-enyl, oct-7-enyl, dec-9-enyl, dodec-11-enyl or octadec-17-enyl, with allyl being preferred.

Preferred compounds of formulae I and II are those wherein $R^3$ and $R^4$ are hydrogen.

Particularly interesting compounds of formula I are those wherein $R^1$ and $R^2$ are each independently of the other hydrogen or $C_1$-$C_{12}$alkyl, $R^3$ and $R^4$ are hydrogen, X is a —$CR^5R^6$—group, and wherein $R^5$ and $R^6$ are each independently of the other hydrogen or methyl.

Interesting compounds of formula I are also those wherein $R^1$, $R^2$, $R^3$ and $R^4$ are hydrogen, and X is a group selected from —$CH_2$—, —$CH(CH_3)$ or —$C(CH_3)_2$—.

Particularly preferred compounds of formula I are those wherein $R^1$ and $R^2$ are each independently of the other a —$CH_2$—$CHR^3$—$CH_2$—S—H group.

Of special interest are also compounds of formula II, wherein $R^3$ is hydrogen, $R^8$ is hydrogen or methyl, —$CR^5R^6$— is a group selected from —$CH_2$—, —$CH(CH_3)$— or —$C(CH_3)_2$—, and wherein n is an integer from 1 to 4

The —CH₂—CHR³—CH₂—S—H groups in the novolak of formular II are preferably in ortho- or para-position with respect to the phenolic hydroxyl group; most preferably in the ortho- position.

R¹ and R² are preferably hydrogen or methyl, with hydrogen being most preferred.

R⁸ is preferably hydrogen.

X is preferably —CH₂— or —C(CH₃)₂—, with —C(CH₃)₂— being most preferred.

Further preferred meanings of the group X are —S— or —SO₂— or 13 (CH₃)C[—CH₂—COOCH₃]13 or —(CH₃)C[—CH₂—CH₂—COOCH₃]—.

The compounds of formula I or II can for example be prepared by reacting a compound of formula III or IV

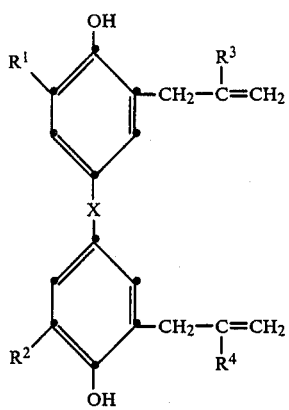

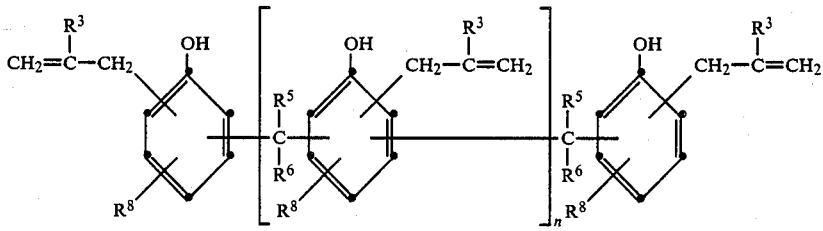

with a molar amount of a thiocarboxylic acid of formula V

(V)

which is substantially proportionate to the content of allylic double bonds, in the presence of a free radical generator followed by a saponification step. In the formulae III, IV and V above, R¹, R², R³, R⁴, R⁵, R⁶, R⁸ and X, as well as the index n, have the meanings as defined above, and R⁹ is a monovalent organic radical, e.g. alkyl, preferably methyl; however, in this case R¹ and R² are —CH₂—CR³=CH₂ instead of —CH₂—CHR³—CH₂—S—H.

If compounds of formula I or II containing alkenyl-methyl radicals R¹, R² or R⁸ are to be prepared, then the compounds of formula III or IV are reacted with a corresponding deficiency of thiocarboxylic acids of formula V.

The novolak of formula IV may also contain small proportions of phenol nuclei which do not contain allyl, e.g. phenol, o-cresol or p-cresol nuclei.

The reaction products (acylthiopropyl derivatives) of formulae VI and VII

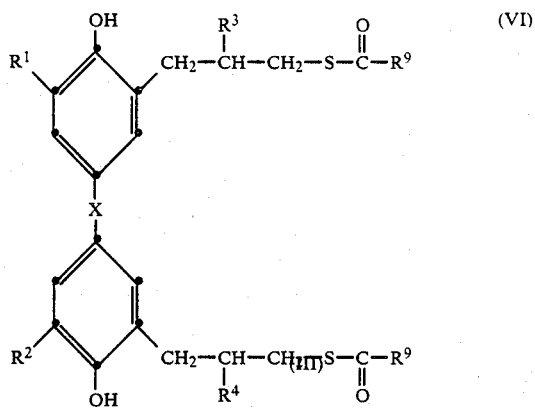

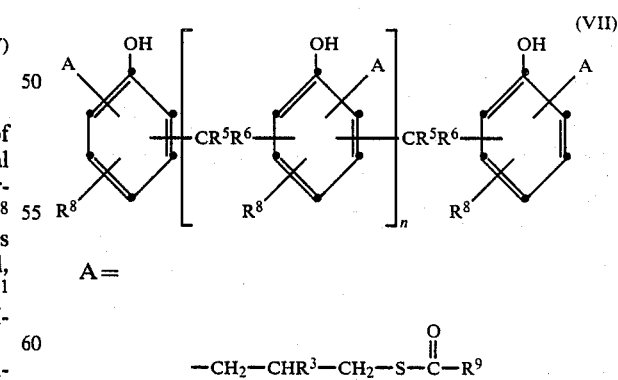

are converted into the mercaptophenols of formulae I and II in a subsequent hydrolysis step in a manner known per se.

The hydrolysis is conveniently effected in a manner known per se under alkaline conditions, for example under the action of aqueous KOH. The compounds of formulae I and II may also be prepared without having to effect said hydrolysis step, i.e. by reacting the compounds of formula III or IV direct with hydroge sulfide in the presence of a free radical generator. Both variants of reactions of this type are described in U.S. Pat. No. 3,336,393.

The bis- or polyallylphenols and bis- or polymethallylphenols of formula III or IV are known compounds or they can be prepared by methods which are known per se, for example by etherification of the corresponding polyphenols with allyl halide and subsequent Claisen rearrangement.

The thiocarboxylic acids of formula V are also known compounds and can likewise be obtained by methods which are known per se. A preferred process comprises reacting a suitable carboxylic acid anhydride, preferably acetic anhydride, with hydrogen sulfide in alkaline aqueous solution, isolating the resultant mixture of carboxylic acid and thiocarboxylic acid and using it, without further separation, in the subsequent reaction with the allylphenol or methylallylphenol.

The amount of thiocarboxylic acid V or hydrogen sulfide employed will depend on the number of allyl or methallyl groups in the starting material III or IV. As a rule, equimolar amounts of thiocarboxylic acid or hydrogen sulfide are used, based on the allyl groups. However, it is entirely possible to use an excess or a less than equivalent amount of thiocarboxylic acid.

Use of a less than equivalent amount of thiocarboxylic acid V will result in only a partial reaction of the allyl groups of compounds III or IV. Such partially thioacylated products, especially partially reacted novolaks IV are also suitable as intermediates for the preparation of mercaptophenols of the invention. The resultant final products also fall within the scope of this invention. These partially reacted novolaks IV are mixtures of compounds of different chain length and differing mercapto group content. On average, at least 50% of the allyl groups of compounds III and IV should be reacted.

The reaction to give the final product I or II or the intermediate VI or VII is induced by radical initiation. This radical initiation is achieved e.g. by exposing the reaction mixture, if desired in the presence of a catalyst, to irradiation with shortwave light, or by heating the mixture, preferably in the presence of a free radical generator.

Illustrative of free radical generators are organic peroxides such as benzoyl peroxide, acetyl peroxide or cumyl hydroperoxide and, in particular, azo compounds. Preferred azo compounds are in particular those in which the azo group is attached on both sides to tertiary carbon atoms which, in addition to carrying alkyl groups, also carry nitrile or ester groups. An important representative of this class of compound is thus e.g. a,a-azobisisobutyronitrile (AIBN).

Exemplary of catalysts which may, if desired, be suitably used for the photoinitiation reaction are benzoin ethers, benzile ketals, $\omega$-dialkoxyacetophenone derivatives or aromatic ketone/amine combinations.

The amount of free radical generator which may be employed is not crucial and may vary within wide limits. It is preferably less than 10 mol % of the number of allyl or methallyl groups in the reaction mixture.

The reaction of compound III and V or IV and V or of compound III or IV with hydrogen sulfide can be carried out in the presence or absence of a solvent.

If a solvent is employed, it must be inert to the reactants and able to dissolve them. Examples of suitable solvents are therefore aliphatic or aromatic hydrocarbons such as hexane, benzene, toluene or xylene; or chlorinated hydrocarbons such as dichloromethane or chlorobenzene; and also ethers such as dioxane or diethyl ether; or aprotic solvents such as dimethylformamide. Depending on the mode of reaction and on the reactants, the reaction temperature is normally in the range from $-10°$ to $250°$ C.

It is preferred to carry out the reaction of the allylphenol with the thiocarboxylic acid in the temperature range from 40° to 80° C. in an inert gas, for example $N_2$, in the absence of a solvent. The radical generator employed in this process variant is preferably azobisisobutyronitrile, although other radical generators are also suitable for the purpose. Subsequently, hydrolysis is effected with aqueous potassium hydroxide solution.

The phenols of this invention can be isolated from the reaction mixture in conventional manner, for example by distillation or fractional crystallization or by extraction, preferably with an aqueous alkaline solution.

The compounds of formula I and II can be employed as hardeners for epoxy resins.

Accordingly, the invention also relates to compositions comprising
(a) an epoxy resin containing on average more than one epoxy group in the molecule or a still fusible and/or soluble curable precondensate of said epoxy resin, and
(b) at least one compound of formula I and/or II, and
(c) optionally, curing accelerators, and to the cured products which can be obtained therefrom by heating.

Preferred compositions are those comprising (a) the epoxy resin and (b) at least one compound of formula I.

The epoxy resins to be employed preferably contain more than one epoxy group in the molecule. Such compounds are in particular:

alicyclic polyepoxides such as epoxyethyl-3,4-epoxycyclohexane, (vinylcyclohexene diepoxide), limonene diepoxide, dicyclopentadiene diepoxide, bis(3,4-epoxycyclohexylmethyl) adipate, (3',4'-epoxycyclohexylmethyl)-3,4-epoxycyclohexanecarboxylate, 3',4'-epoxy-6'-methylcyclohexylmethyl-3,4-epoxy-6-methylcyclohexanecarboxylate, 3-(4',4'-epoxycyclohexyl)-2,4-dioxaspiro[5,5]-8,9-epoxyundecane, 3-(glycidyloxyethoxyethyl)-2,4-dioxaspiro-[5.5]-8,9-epoxyundecane;

di- or polyglycidyl ethers of polyhydric aliphaic alcohols such as 1,4-butanediol, or polyalkylene glycols such as polypropylene glycols; di- or polyglycidyl ethers of cycloaliphatic polyols such as 2,2-bis(4-hydroxycyclohexyl)propane; di- or polyglycidyl ethers of polyhydric phenols such as resorcinol, bis(4-hydroxyphenyl)methane (bisphenol F), 2,2-bis(4-hydroxyphenyl)propane (bisphenol A), 2,2-bits(4'-hydroxy-3',5'-dibromophenyl)propane, 1,1,2,2,-tetrakis(4'-hydroxyphenyl)ethane, or condensates of phenols with formaldehyde which are obtained under acid conditions, such as phenol novolaks and cresol novolats; and also di- or poly(8-methylglycidyl)ethers of the above polyalcohols and polyphenols;

polyglycidyl esters and poly($\beta$-methylgl) esters of polyvalent carboxylic acids such as phthalic acid, terephthalic acid, tetrahydrophthalic acid or hexahydrophthalic acid;

N-glycidyl derivatives of amines, amides and heterocyclic nitrogen bases such as N,N-diglycidyl aniline, N,N.-diglycidyl toluidine, N,N,N',N'-tetraglycidyl bis(4-aminophenyl)methane, triglycidyl isocyanurate, N,N'-diglycidyl ethyl urea, N,N'-diglycidyl-5,5-dimethylhydantoin, N,N'-diglycidyl-5-isopropylhydantoin, N,N'-diglycidyl-5,5-dimethyl-6-isopropyl-5,6-dihydrouracil.

Particularly preferred are polyglycidyl ethers of phenol/formaldehyde or cresol/formaldephyde novolaks as well as diglycidyl ethers of bisphenol A and bisphenol F.

Examples of suitable catalysts (accelerators) are basic organic compounds such as primary and/or secondary amines, e.g. N,N-dimethyl-1,7-diamino-4-azaheptane, or tertiary amines, salts or quaternary ammonium compounds thereof, e.g. benzyl dimethylamine, 2,4,6-tris(-dimethylaminomethyl)phenol, 1-methylimidazole, 2-ethyl-4-methylimidazole, 2-phenylimidazole, 4-aminopyridine, tripentylammonium phenolate; or alkali metal alcoholates, e.g. sodium hexane triolate.

In particular in combination with strong organic bases such as tetrabutylammonium hydroxide, the compounds of formulae I and II can be employed for curing epoxy resins at low temperatures.

The reaction (curing) of the compositions of the invention is conveniently carried out in the temperature range from $-25°$ C. to $200°$ C., preferably from $25°$ C. to $180°$ C.

Preferred curing catalysts are 2-phenylimidazole, N,N-dimethylbenzylamine or 2,4,6-tris(dimethylaminomethyl)phenol.

Curing can be carried out in known manner in two or more steps, the first step being carried out at low temperature (room temperature) and the postcuring at more elevated temperature.

Two-step curing is normally carried out by first discontinuing the curing reaction prematurely, i.e. performing the first step at room temperature or slightly elevated temperature, when a still fusible and/or soluble curable precondensate (B-stage) is obtained from the epoxy component (a) and the hardener component (b). Such a precondensate can be used e.g. for making prepregs, moulding compounds or sintering powders.

The compositions of this invention comprising a) an epoxy resin containing on average more than one epoxy group in the molecule, (b) at least one compound of formula I or II form soluble B-stages if these resin/hardener compositions are stored at room temperature. Such compositions are storage stable over prolonged periods of time (days) and can thus be further processed in suitable manner.

The term "curing" as employed throughout this specification denotes the conversion of the soluble, either liquid or fusible, epoxy resins into solid insoluble and infusible three-dimensional crosslinked products or moulding materials, usually with concomitant shaping to moulded articles such as castings, mouldings and laminates, impregnations, coatings, varnish films or bonds.

The compositions of this invention can be prepared by simple stirring of the components and cautiously warming the components until dissolved. If a solid epoxy resin is used, this is temporarily heated to the melt and then the hardener and, optionally, the curing accelerator and/or other additives are dissolved in the melt.

Customary modifiers such as extenders, fillers and reinforcing agents, pigments, dyes, plasticisers, flow control agents, thixotropic agents, flexibilisers, flame retardants or mould release agents, can also be added, in any phase, to the curable mixtures of the present invention before curing.

Typical examples of extenders, reinforcing agents, fillers and pigments which may be added to the curable mixtures of this invention are: coal tar, bitumen, liquid coumarone/indene resins, textile fibres, glass fibres, asbestos fibres, boron fibres, carbon fibres, cellulose, polyesters, polyamides, polyethylene powder, polypropylene powder, wood powder, quartz powder, mineral silicates such as mica, asbestos powder, slate powder, kaolin, silica aerogel, lithopones, barytes, titanium dioxide, carbon black, graphite, oxide colours such as iron oxide, or metal powders such as aluminium powder or iron powder.

Examples of suitable plasticisers for modifying the curable compositions are dibutyl phthalate, dioctyl phthalate and dinonyl phthalate, tricresyl phosphate, trixylenyl phosphate and diphenoxyethylformal.

Examples of flow control agents which can be added when the curable mixtures are used in particular in surface protection are silicones, liquid acrylic resins, cellulose acetobutyrate, polyvinylbutyrate, waxes or stearates (some of which are also used as mould release agents).

Examples of suitable flexibilisers are oligoester segments, polyesters, thermoplasts and butadiene/acrylonitrile oligomers such as Hycar ® (a product of Goodrich).

The curable mixtures of this invention are distinguished by good adhesion to metals, high deflection temperatures and also good resistance to moisture and chemicals.

The curable mixtures of this invention are used, in particular, in the fields of surface protection, electrical engineering, laminating processes and adhesives technology and in the building trade. They can be used in a formulation suited in each case to the particular application, in the unfilled or filled state, if desired in the form of solutions or emulsions, as paints, solvent-free coatings, whirl sintering powders, moulding compositions, injection moulding compositions, impregnating resins, casting resins, foams, adhesives, films, sheets, bonding agents, tooling resins, laminating resins, sealing and trowelling compounds, flooring compositions, and as binders for mineral aggregates.

In particular, the present invention relates to the use of compositions containing a) an epoxy resin comprising on average more than one epoxy group in the molecule, and b) at least one compound of the formula I and/or II as adhesives.

PREPARATORY EXAMPLES

1. Preparation of 2,2'-bis(3-(3-mercaptopropyl-4-hydroxyphenyl)propane (1a) o,o'-Bis(3-acetylthiopropyl) bisphenol A 666.8 g of 2,2-bis(3-allyl-4-hydroxyphenyl)propane are placed in a reaction vessel equipped with a stirrer, dropping funnel and $N_2$ inlet and heated to $75°$ C. under $N_2$ gas. 4.92 g of azobisisobutyronitrile (AIBN) are then added and, through the dropping funnel, 780 g thioacetic acid are added over one hour. The temperature of the reaction mixture is maintained at $75°$ C. and 3 further 4.92 g portions of azobisisobutyronitrile are added every 20 minutes until a total of 19.68 g of AIBN has been added. The mixture is stirred at $75°$ C. under $N_2$ for 4 hours. A final portion of 4.92 g of azobisisobutyronitrile is added and the mixture is stirred for a further 3 hours. The product is then evaporated in a rotation vacuum evaporator (rotavap) to give 1036 g of a yellow paste.

|  | (a) Elementary analysis: | | |
|---|---|---|---|
|  | C | H | S |
| theory % | 65.19 | 7.00 | 13.92 |
| found % | 64.5 | 6.96 | 13.2 |

(b) 100 MHz $^1$H-NMR spectrum: Absence of olefinic proton peaks in the 5-6 ppm region (standard: TMS) indicate the complete disappearance of the allylic group
Peaks at:
2.3 ppm (3 protons; —S—CO—CH$_3$)
1.8 ppm (2 protons; —S—C13 CH$_2$—C—phenyl)
2.6 ppm (2 protons; —S—CH$_2$—C—C-phenyl)
2.8 ppm (2 protons; —S—C—C—CH$_2$—phenyl).

(1b) Purification of the crude product of Example (1a)
360.8 g of the crude pasty product of Example 1a) are dissolved in 100 ml of hot xylene. 1 g of active charcoal is added and the solution is filtered and allowed to crystallize at 5° C. The crystals are filtered and dried under vacuum at 100° C. (50 mbar), affording 142 g of white crystals having a melting point of 118.1°–119.5° C.

|  | Elementary analysis: | | | |
|---|---|---|---|---|
|  | C | H | S | O |
| calculated % | 65.19 | 7.00 | 13.92 | 13.89 |
| found % | 65.88 | 7.07 | 13.43 | 13.79 |

(1c) o,o′-Bis(3-mercaptopropyl) bisphenol A
50 g of the product of Example (1a), purified in accordance with Example (1b), are added to a solution of 44.1 g of KOH in 200 ml of a mixture of ethanol and water (50:50 parts by volume). The mixture is kept at 50° C. for 1 hour and then boiled under reflux for 1 hour at about 80° C. After the mixture has cooled to room temperature, it is adjusted to a pH of 6–7 with 37.5% hydrochloric acid and extracted with 1 l of dichloromethane. The organic phase is separated and dried over sodium sulfate, and the solvent is drawn off in a rotation evaporator to give 36.4 g of a slightly yellow resinuous liquid (yield: 38.9% of theory, based on acylated product).

Analytical data

|  | (a) Elementary analysis | |
|---|---|---|
|  | C | H |
| calculated % | 66.98 | 7.49 |
| found % | 67.2 | 7.42 |

(b) Thiol content (determined by iodometric titration)
4.60 —SH equivalents/kg
(c) $^1$H-NMR spectrum (250 MHz)

| 6.5–7 ppm (m) | 6 aromatic protons |
| 5.2 ppm (s) | 2 phenolic protons |
| 2.5–2.9 ppm (m) | 8 aliphatic protons (—CH$_2$—CH$_2$—phenyl) |
| 1.75–2.1 ppm (m) | 4 aliphatic protons (—C—CH$_2$—S—) |
| 1.6 ppm (s) | 6 aliphatic protons (—C(CH$_3$)$_2$—) |
| 1.4 ppm (m) | 2-thiol protons |

2. Preparation of a novolak based on formaldehyde and 2-mercaptopropylphenol

2a) Preparation of an (o-acetylthiopropyl)phenol/-formaldehyde novolak
Following the procedure of Example 1a), 419.9 g of a 2-allylphenol/formaldehyde novolak (prepared by condensation of 1 part of formaldehyde with 6 parts of 2-allylphenol; allyl group content: 2.36 val) are reacted at 80° C., under nitrogen, with 179.9 g (2.36 moles) of thioacetic acid and 10.2 g of azobisisobutyronitrile. The azobisisobutyronitrile is added in 5 equal portions of 2.04 g. Yield: 589.2 g of product (98.2% of theory).
The $^1$H-NMR peaks (250 MHz) of the allyl protons of the starting material in the 5.1–5.2 ppm and 5.9–6.1 ppm range (against TMS) have disappeared from the $^1$H-NMR spectrum of the final product. Instead a peak of the protons of the acetyl group appears (at 2.3 ppm).

(2b) Purification of the crude product
200 ml of dichloromethane and 220 ml of aqueous ethanol (water content: 30% by volume) are added to 177.2 g of the crude product of Example (2a) and the supernatant phase is removed by decantation. A further 220 ml of aqueous ethanol and 100 ml of water are added and again the supernatant phase is removed by decantation. The residual novolak is washed with two 230 ml portions of water and dried over Na$_2$SO$_4$. The product is subsequently dried again at 40° C. (17 mm Hg) and at 60° C. (3 mm Hg) in a rotary evaporator. Yield: 164 g of purified final product. As determined by GPC, said product has molecular weights of 527 (number average) and 597 (weight average) respectively.

(2c) Saponification of the acetylated product to give mercaptan
50 g of the product of Example (2a), purified in accordance with Example (2b), are placed in a reaction vessel. A solution of 22.4 g (0.4 mol) of potassium hydroxide in 200 ml of a mixture of ethanol and water (50:50 parts by volume) is added. The mixture is allowed to react for about 1 1/2 hours at 50° C. and is subsequently boiled under reflux for 2 hours. After the mixture has cooled to room temperature, it is neutralised with 15 ml of 37.5% hydrochloric acid. The precipitate is isolated by filtration, extracted with 350 ml of dichloromethane and dried over Na$_2$SO$_4$. After filtration, the solvent is drawn off, affording 37.65 g of a viscous resinuous product.
Mercaptan content
(titrimetrically determined):
  4.04 equiv./kg
  (theory: 4.07 equiv./kg).
Molecular weight
(determined by GPC analysis):
  $\overline{M}_n = 484$;
  $\overline{M}_n = 569$.

APPLICATION EXAMPLES

Example A

An adhesive formulation consisting of 100 parts by weight of a liquid epoxy resin based on bisphenol A (epoxide value: 5.25 val/kg), 49.8 parts by weight of the hardener of Example (1c) and 0.02 parts by weight of 2-phenylimidazole as curing accelerator is prepared by mixing the components at 60° C.

Adhesive bonds are then prepared with this formulation between aluminum surfaces. This is done by punching bore holes of a specific diameter and specific depth in an aluminum plate and filling them with the resin mixture. Aluminum cylinders of specific diameter are then fixed on this substrate.

The adhesive bonds are then cured for 2 hours at 120° C., 2 hours at 150° C. and 2 hours at 180° C.

Measurement of the adhesive bond is made with a Twistometer (q.v. Adhesion 3, edited by K.W. Allen; Applied Science Publishers Ltd.; Barking (Essex); 1978).

To this end the aluminium base plate is made fast and a specific torsional force is exerted on the aluminium cylinder by means of a lever arm. The adhesion can be ascertained from the maximum torsional force resulting in rupture of the adhesive bond.

An adhesion of 70.1 N/mm² is measured.

Example B

An adhesive formulation consisting of 100 parts by weight of liquid epoxy resin (diglycidyl ether based on bisphenol A; epoxide content: 5.3 val/kg), 41.8 parts by weight of 2,2'-bis(3-mercaptopropyl)bisphenol A according to Example 1c) and 2.2 parts by weight of N,N-dimethyl-1,7-diamino-4-azaheptane as curing accelerator is prepared by mixing the components at room temperature. Al/Al bonds are then prepared with this formulation. The adhesive bonds are cured by subjecting them to heat for 30 minutes at 180° C.

As a criterion of the quality of the adhesive bond, the shear strength (on Anticorodal B) is determined in accordance with DIN 53283. A value of 22.4 N/mm² is measured.

Example C

An adhesive formulation consisting of 100 parts by weight of liquid epoxy resin (diglycidyl ether based on bisphenol A; epoxide content: 5.3 val/kg), 44.0 parts by weight of 2,2'-bis(3-mercaptopropyl)bisphenol A according to Example (1c) and 0.25 parts by weight of 2-phenylimidazole as curing accelerator is prepared by mixing the components at 60° C.

Al/Al bonds are then prepared with this formulation. The curing of the adhesive bonds and the measurement of the shear strength are carried out in accordance with the procedure described in Example B. A shear strength of 8.6 N/mm² is measured.

What is claimed is:

1. A composition comprising
   (a) an epoxy resin containing on average more than one epoxy group in the molecule, and
   (b) a compound of formula I or II

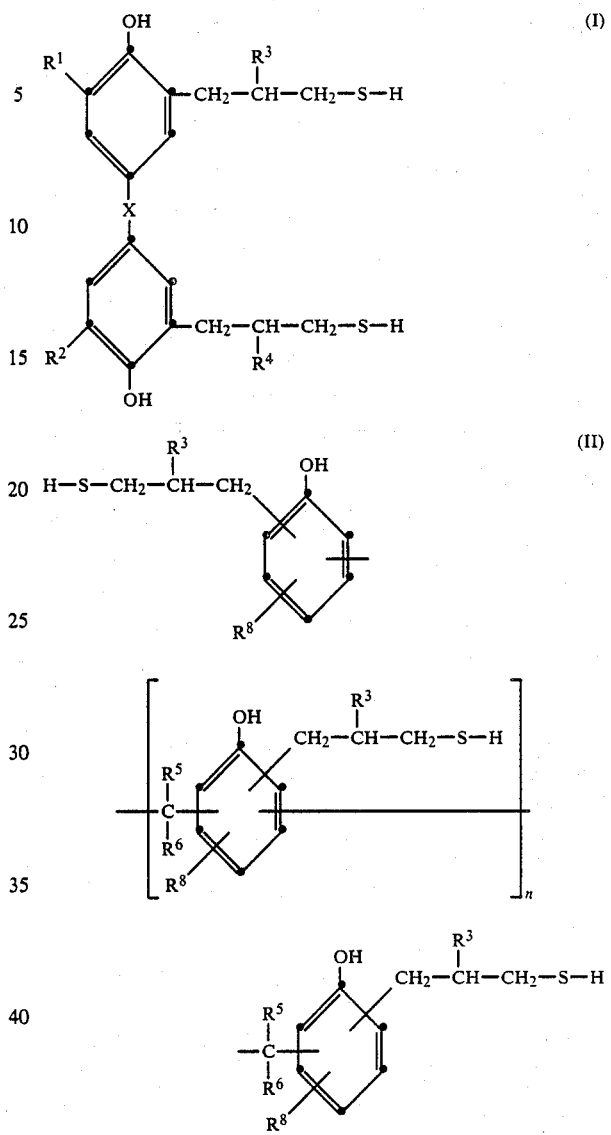

in which formulae $R^1$ and $R^2$ are each independently of the other hydrogen, $C_1$-$C_{18}$ alkyl, $C_3$-$C_{18}$ alkenylmethyl, cyclohexyl, phenyl, benzyl or tolyl, or are a —$CH_2$—$CHR^3$—$CH_2$—S—H group, $R^3$ and $R^4$ are each independently of the other hydrogen or methyl, X is —$CR^5R^6$—, —S—, —SO—, —$SO_2$— or —($CH_3$)C[—($CH_2$-$)_m$—$COOR^7$]—, $R^5$ and $R^6$ are each independently of the other hydrogen or $C_1$-$C_6$ alkyl, $R^7$ is $C_1$-$C_{18}$-alkyl, $R^8$ is hydrogen, $C_1$-$C_{18}$ alkyl, $C_3$-$C_{18}$ alkenylmethyl or phenyl, m is 1 or 2 and n is an integer from 1 to 10, or a mixture of such compounds.

2. A cured product obtainable by heating a composition as claimed in claim 1.

* * * * *